(12) United States Patent
Takahashi et al.

(10) Patent No.: US 7,981,100 B2
(45) Date of Patent: Jul. 19, 2011

(54) DISPOSABLE ABSORBENT ARTICLE

(75) Inventors: Yuki Takahashi, Tokushima (JP);
Masaru Fujioka, Tokushima (JP)

(73) Assignee: Livedo Corporation, Ehime (JP)

( * ) Notice: Subject to any disclaimer, the term of this patent is extended or adjusted under 35 U.S.C. 154(b) by 155 days.

(21) Appl. No.: 12/472,692

(22) Filed: May 27, 2009

(65) Prior Publication Data

US 2009/0299319 A1 Dec. 3, 2009

(30) Foreign Application Priority Data

May 27, 2008 (JP) .................................. 2008-138483

(51) Int. Cl.
*A61F 13/15* (2006.01)
(52) U.S. Cl. ......... 604/385.25; 604/385.22; 604/385.23; 604/385.24; 604/385.26; 604/385.27; 604/385.29; 604/385.3; 604/396
(58) Field of Classification Search ............. 604/385.22, 604/385.23, 385.24, 385.25, 385.26, 385.27, 604/385.29, 385.3, 396
See application file for complete search history.

(56) References Cited

U.S. PATENT DOCUMENTS

| 5,147,487 A | 9/1992 | Nomura et al. |
| 5,334,152 A | 8/1994 | Nomura et al. |
| 2008/0071241 A1 | 3/2008 | Bittner et al. |

FOREIGN PATENT DOCUMENTS

| EP | 0 626 161 | 11/1994 |
| EP | 1 300 124 | 4/2003 |
| EP | 1 834 617 | 9/2007 |
| JP | 3-33201 | 2/1991 |
| JP | 6-197925 | 7/1994 |
| WO | 2006/000303 | 1/2006 |

OTHER PUBLICATIONS

European Search Report issued Jul. 24, 2009 in Application No. EP 09 00 6416.

*Primary Examiner* — Jacqueline F Stephens
(74) *Attorney, Agent, or Firm* — Wenderoth, Lind & Ponack L.L.P.

(57) ABSTRACT

A disposable absorbent article includes a sheet member, an absorbent core, at least one front leg elastic member, and at least one rear leg elastic member. The leg elastic members intersect at left and right intersections located in a crotch region of the sheet member. The left and right intersections are placed at any position on the outer side in the lateral direction relative to the vicinity of left and right side edges of the absorbent core in the crotch region. The front leg elastic member has left and right front leg contraction-reduced sections located on the outer side in the lateral direction relative to the left and right intersections. The left and right front leg contraction-reduced sections are cut so as to have reduced contractile forces. The rear leg elastic member has left and right front leg contraction-reduced sections located on the outer side in the lateral direction relative to the left and right intersections. The left and right rear leg contraction-reduced sections are cut so as to have reduced contractile forces.

5 Claims, 5 Drawing Sheets

DISPOSABLE ABSORBENT ARTICLE

BACKGROUND OF THE INVENTION

1. Field of the Invention

The present invention relates to a disposable absorbent article to be applied, when worn, to a region including the wearer's crotch.

2. Description of the Background Art

Most disposable absorbent articles have elastic members attached in a stretched state along leg-side edges in order to prevent leakage of bodily discharges such as urine through the leg openings. However, the greater the contractile forces of the elastic members, the higher the degree of shrinkage of the leg openings. Then, it may be difficult for the wearer or care giver to pull the absorbent article up and down. In addition, excessively great contractile forces of the elastic members attached along the leg-side edges may give the wearer an excessively tight and uncomfortable fit. Particularly in the case of a garment-type absorbent article, it is difficult for the wearer to insert his/her legs into the leg openings, if they shrink excessively due to the contractile forces of the elastic members attached along the leg-side edges.

For example, to prevent leakage of bodily discharges such as urine and to ensure the absorbing capacity of an absorbent core, the crotch region needs to have a width to a certain degree. Accordingly, the crotch region of the absorbent article is likely to be wide in the lateral direction when worn, so that pulling the absorbent article up and down may become difficult. If the crotch region of the absorbent article is excessively wide in the lateral direction, it may provide a discomfort for the wearer. Particularly in the case of a garment-type absorbent article, if the crotch region is excessively wide in the lateral direction, it reduces the left and right leg openings in size, thus making it difficult to insert the wearer's legs into the leg openings.

A conventional disposable absorbent article with elastic members provided along the leg-side edges is described in, for example, European Patent Publication No. EP 1834617 A2. The absorbent article disclosed in this document has front and rear elasticated sections (38) along the leg-side edges of the absorbent article, with part of the elasticated sections (38) being cut up (cf. paragraph [0025] and FIG. 1). Accordingly, unelasticated sections (46) are provided at two each positions on the left and right sides along the leg-side edges of the absorbent article. In addition, since the front and rear elasticated sections (38) cross the crotch region of the absorbent article while being spaced from each other in the front-to-rear direction, unelasticated peripheral sections (49) are also provided along the leg-side edges at locations corresponding to the crotch region. By the presence of these unelasticated sections (46) and (49), the portions of the absorbent article along the leg-side edges provide a soft feeling to the wearer, and offer improved breathability.

In the absorbent article described in the above document, however, the front and rear elasticated sections (38), crossing the crotch region of the absorbent article while being spaced from each other in the front-to-rear direction, may exert insufficient contractile forces on the crotch region in the lateral direction. With such insufficient lateral contraction on the crotch region, the crotch region is more likely to be widened in the lateral direction, and the front and rear elasticated sections (38) do not exert their contractile forces on the left and right portions of the crotch region. This may result in clearances formed between the crotch region of the absorbent article and the wearer's crotch region, causing leakage of bodily discharges such as urine through the clearances.

Another conventional absorbent article is arranged such that front and rear elastic members provided along the leg-side edges overlap each other in the crotch region. With this arrangement, the crotch region is expected to receive sufficient contractile forces in the lateral direction. However, the elastic members, provided continuously along the leg-side edges, may produce an excessively tight fit.

SUMMARY OF THE INVENTION

It is an object of the present invention to provide a disposable absorbent article that exerts effective contraction on the crotch region while relaxing contraction along the leg-side edges to an appropriate degree, facilitates pulling up and down, and allows the left and right portions of the crotch region of the absorbent article to fit appropriately to the wearer's crotch region.

A first aspect of the present invention is directed to a disposable absorbent article to be applied, when worn, to a region including a crotch region of a wearer. The disposable absorbent article includes a sheet member to be applied to a region at least including a front waist region, the crotch region and a rear waist region of the wearer, an absorbent core provided inside the sheet member or on a skin-facing side of the sheet member for absorbing bodily fluids discharged from the wearer, at least one front leg elastic member attached in a stretched state along a path from one front end of one of left and right leg-side edges of the sheet member, crossing a crotch region of the sheet member, and leading to the other front end of the other of the left and right leg-side edges, and at least one rear leg elastic member attached in a stretched state along a path from one rear end of one of the left and right leg-side edges of the sheet member, crossing the crotch region of the sheet member, and leading to the other rear end of the other of the left and right leg-side edges. The front leg elastic member and the rear leg elastic member intersect at left and right intersections located in the crotch region of the sheet member. The left and right intersections are placed at any position on the outer side in the lateral direction relative to the vicinity of left and right side edges of the absorbent core in the crotch region of the sheet member. The front leg elastic member has left and right front leg contraction-reduced sections located on the outer side in the lateral direction relative to the left and right intersections. The left and right front leg contraction-reduced sections have reduced contractile forces by cutting up. The rear leg elastic member has left and right front leg contraction-reduced sections located on the outer side in the lateral direction relative to the left and right intersections. The left and right rear leg contraction-reduced sections have reduced contractile forces by cutting up.

According to the first aspect, a disposable absorbent article can be provided, as will be described below, that exerts effective contraction on the crotch region while relaxing contraction along the leg-side edges to an appropriate degree, facilitates pulling up and down, and allows the left and right portions of the crotch region of the absorbent article to fit appropriately to the wearer's crotch region.

More specifically, according to the first aspect, at least one front leg elastic member is attached in a stretched state along the path from one front end of one of the left and right leg-side edges of the sheet member, crossing the crotch region of the sheet member, and leading to the other front end of the other of the left and right leg-side edges. At least one rear leg elastic member is attached in a stretched state along the path from one rear end of one of the left and right leg-side edges of the sheet member, crossing the crotch region of the sheet member, and leading to the other rear end of the other of the left and right leg-side edges. The front leg elastic member and the rear leg elastic member intersect at left and right intersections located in the crotch region of the sheet member. Accordingly, the lateral contractile force of the front leg elastic member and that of the rear leg elastic member cooperate together.

Particularly, according to the first aspect, the left and right intersections are placed at any position on the outer side in the lateral direction relative to the vicinity of left and right side edges of the absorbent core in the crotch region of the sheet member. The contraction of the elastic members is less likely to act effectively upon a fibrous assembly constituting the absorbent core due to the high rigidity of the assembly. Therefore, in the crotch region of the absorbent article, the contraction effect of the elastic members in the lateral direction is expected to act particularly upon the laterally outer portions relative to the vicinity of the left and right side edges of the absorbent core. In this respect, the first aspect allows the lateral contraction of the front and rear leg-side elastic members to act effectively upon the laterally outer portions relative to the vicinity of the left and right side edges of the absorbent core in the crotch region of the absorbent article.

Accordingly, the portions of the front and rear leg-side elastic members that cross the crotch region exert sufficient contraction on the crotch region in the lateral direction. This in result effectively prevents the crotch region of the absorbent article from being widened in the lateral direction, which facilitates pulling the absorbent article up and down. The prevention of lateral widening of the crotch region of the absorbent article reduces a wearer's discomfort at the crotch region. In the case of a garment-type absorbent article, for example, the prevention of lateral widening of the crotch region enlarges the left and right leg openings, which makes it easier for the wearer to insert his/her legs into the leg openings.

Further, according to the first aspect, the front leg elastic member has left and right front leg contraction-reduced sections located on the outer side in the lateral direction relative to the left and right intersections. The left and right front leg contraction-reduced sections have reduced contractile forces by cutting up. The rear leg elastic member has left and right front leg contraction-reduced sections located on the outer side in the lateral direction relative to the left and right intersections. The left and right rear leg contraction-reduced sections have reduced contractile forces by cutting up. The presence of these front and rear leg contraction-reduced sections at the four positions relaxes appropriately the degree of contraction of the front and rear leg elastic members along the leg-side edges of the absorbent article. As a result, excessive shrinkage of the leg openings is reduced to an appropriate degree, and the leg openings are more likely to be enlarged to facilitate pulling up and down of the absorbent article. In addition, the appropriate relaxation of contraction of the front and rear leg elastic members attached along the leg-side edges provides the wearer with a soft fit. In the case of a garment-type absorbent article, for example, the leg openings are prevented from shrinking excessively, which makes it easier for the wearer to insert his/her legs into the leg openings.

Furthermore, according to the first aspect, the front leg elastic member and the rear leg elastic member intersect at left and right intersections located in the crotch region of the sheet member. The left and right intersections are placed at any position on the outer side in the lateral direction relative to the vicinity of the left and right side edges of the absorbent core in the crotch region of the sheet member. This allows the front and rear leg elastic members to exert their contractile forces effectively upon the left and right portions of the crotch region of the absorbent article (particularly on the laterally outer portions relative to the vicinity of the left and right side edges of the absorbent core). As a result, the left and right portions of the crotch region of the absorbent article fit appropriately to the wearer's crotch region. Therefore, clearances that may cause leakage of bodily discharges such as urine therethrough are less likely to be formed between the left and right sides of the crotch region of the absorbent article and the wearer's crotch region.

According to a second aspect of the present invention, in the disposable absorbent article of the first aspect, the left and right intersections are positioned on the outer side in the lateral direction relative to the left and right side edges of the absorbent core.

The second aspect ensures that the front and rear leg-side elastic members exert their contractile forces on the portions of the crotch region of the absorbent article where contraction by the leg-side elastic members is particularly effective (on the laterally outer portions relative to the vicinity of the left and right side edges of the absorbent core).

According to a third aspect of the present invention, in the disposable absorbent article of the first or second aspect, the front leg elastic member further includes a first crotch contraction-reduced section located at any position between the left and right intersections. The first crotch contraction-reduced sections have reduced contractile forces by cutting up. The rear leg elastic member further includes a second crotch contraction-reduced section located at any position between the left and right intersection. The second crotch contraction-reduced sections have reduced contractile forces by cutting up.

According to the third aspect, the first and second crotch contraction-reduced sections are located at any position between the left and right intersections. The presence of these crotch contraction-reduced sections effectively relaxes the contractile forces exerted on the crotch region of the absorbent article (particularly on the laterally inner portion relative to the vicinity of the left and right side edges of the absorbent core). Disadvantages can therefore be avoided such as twisting of the crotch region of the absorbent article and excessive contractile forces exerted on the absorbent core that may reduce the absorbing capability of the absorbent core.

Further, the front and rear leg-side elastic members exert their contractile forces at the intersections where the leg-side elastic members intersect each other. Thus, the front and rear leg-side elastic members maintain their contractile forces on the left and right portions of the crotch region of the absorbent article (particularly on the portions located on the outer side relative to the vicinity of the left and right edges of the absorbent core), while the contractile forces exerted on the crotch region of the absorbent article (particularly on the laterally inner portions relative to the vicinity of the left and right side edges of the absorbent core) can be effectively relaxed, as described above.

According to a fourth aspect of the present invention, in the disposable absorbent article of the third aspect, the first crotch contraction-reduced section ranges over an entire portion of the front leg elastic member provided on the laterally inner side relative to the vicinity of the left and right leg-side edges of the absorbent core. The second crotch contraction-reduced section ranges over an entire portion of the rear leg elastic member located on the laterally inner side relative to the vicinity of the left and right leg-side edges of the absorbent core.

The fourth aspect ensures that the contractile forces exerted on the crotch region of the absorbent article where the absorbent core is located can be effectively relaxed. Disadvantages can therefore be avoided with more reliability such as twisting of the crotch region of the absorbent article and excessive contractile forces exerted on the absorbent core that may reduce the absorbing capability of the absorbent core.

According to a fifth aspect of the present invention, the disposable absorbent article of any one of the first to fourth aspects further includes an inner cover provided on the skin-facing side of the sheet member to be applied at least to the crotch region of the wearer. The absorbent core is provided for the inner cover.

The fifth aspect provides an absorbent article of high quality that can avoid disadvantages such as the absorbent core obstructing or being damaged while applying the front and rear leg-side elastic members to the sheet member, while forming the leg contraction-reduced sections in the leg-side elastic members, and the like.

According to a sixth aspect of the present invention, in the disposable absorbent article of any one of the first to fifth aspects, the sheet member forms a waist opening and left and right leg openings when joining a left edge of a front section and a left edge of a rear section, and joining a right edge of the front section and a right edge of the rear section.

According to the sixth aspect, a disposable absorbent article can be obtained that exerts effective contraction on the crotch region while relaxing contraction along the leg-side edges to an appropriate degree, facilitates pulling up and down, and allows the left and right portions of the crotch region of the absorbent article to fit appropriately to the wearer's crotch region.

DETAILED DESCRIPTION OF THE INVENTION

In the following, a disposable absorbent article according to embodiments of the present invention will be described with reference to the accompanied drawings.

Figure 1:
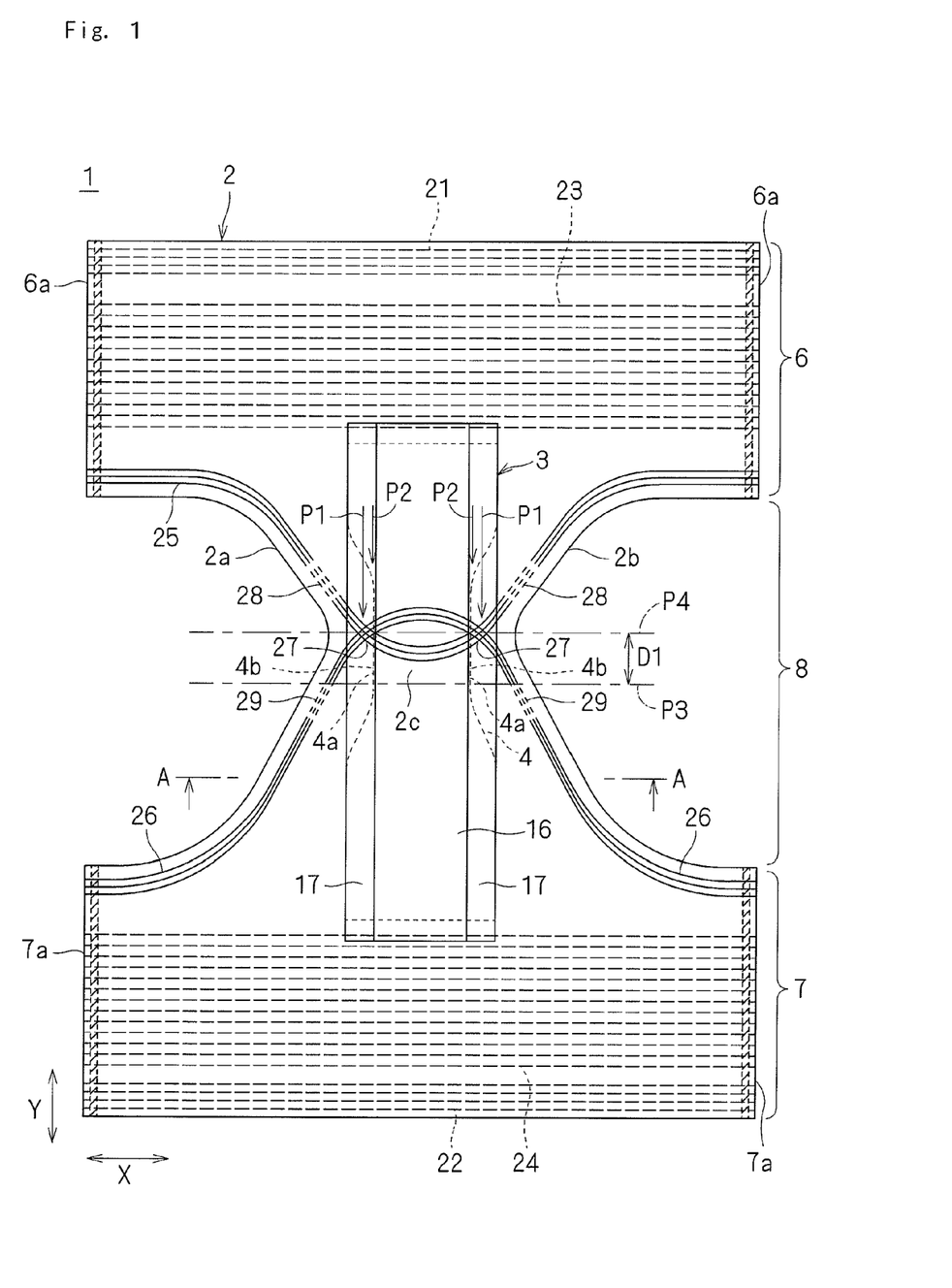
FIG. 1 is a plan view of a disposable absorbent article according to a first embodiment of the present invention, substantially in a flat-out, open state with left and right side joint parts separated.
Figure 2:
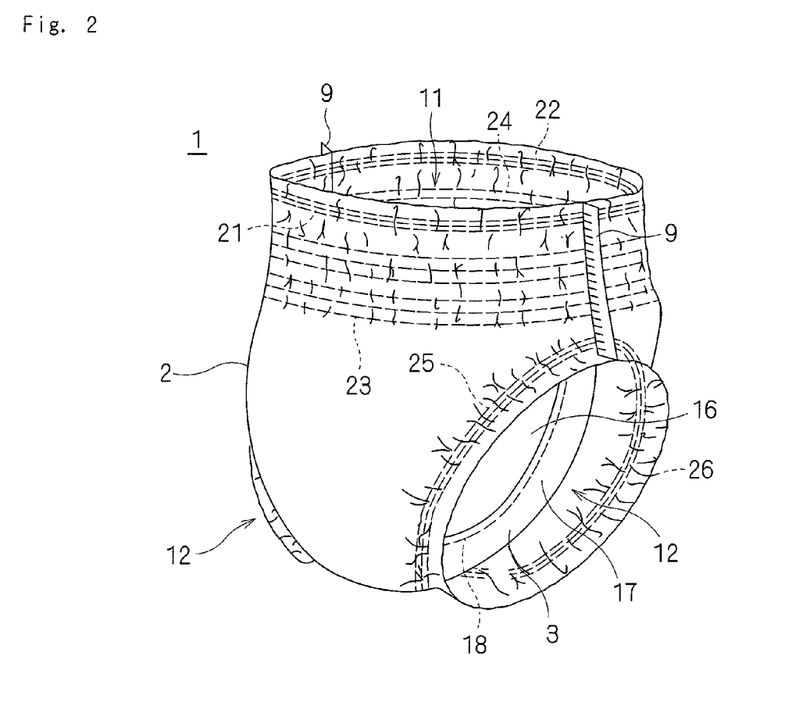
FIG. 2 is a perspective view of the disposable absorbent article shown in FIG. 1 before separation.
Figure 3:
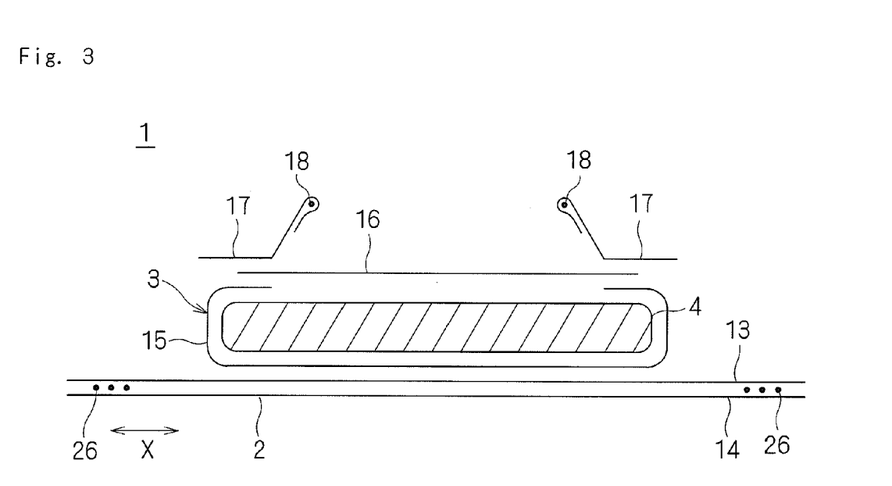
FIG. 3 is a schematic sectional view of a cross-sectional structure taken along the line A-A in FIG. 1.
Figure 4:
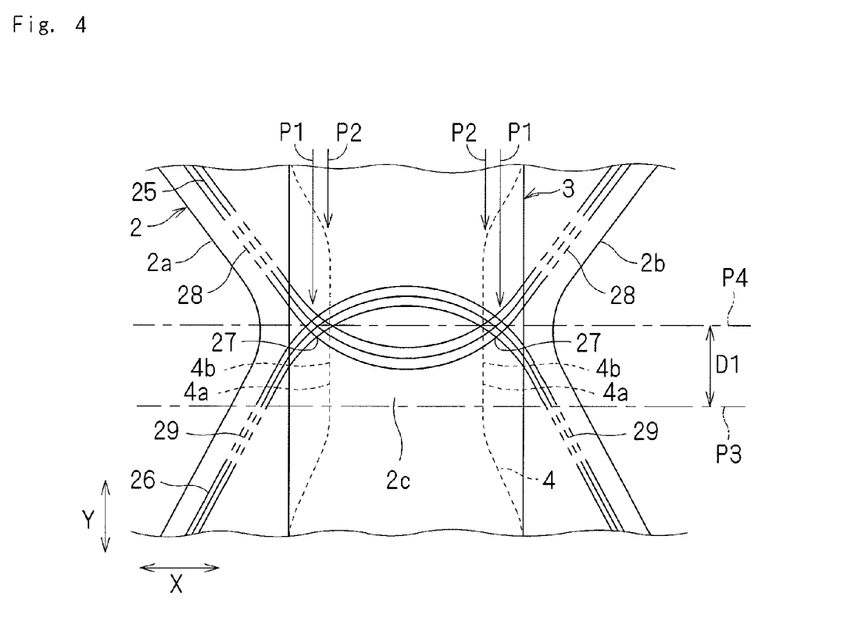
FIG. 4 is a partially enlarged view of the structure shown in FIG. 1.

FIG. 1 is a front view of a disposable absorbent article (hereinafter briefly referred to as an "absorbent article") according to a first embodiment of the present invention, substantially in a flat-out, open state with left and right side joint parts separated. FIG. 2 is a perspective view of the absorbent article shown in FIG. 1 before separation. FIG. 3 is a schematic sectional view of a cross-sectional structure taken along the line A-A in FIG. 1. FIG. 4 is a partially enlarged view of the structure shown in FIG. 1.

In FIGS. 1 to 4 and other figures which will be mentioned later, the longitudinal direction Y corresponds to the front-to-rear or top-to-bottom direction of a wearer. This also applies to the term "longitudinal/longitudinally". The lateral direction X corresponds to the wearer's side-to-side direction. This also applies to the term "lateral/laterally". In FIGS. 1 and 4 to 8, front leg-side elastic members 25 and rear leg-side elastic members 26 are indicated by solid lines for the sake of clarity, although they could essentially be indicated by broken lines as they are actually disposed inside an outer cover 2. In addition, left and right side sheets 17 of an inner cover 3 are not shown in FIGS. 4, 5, 7 and 8 for the sake of clarity.

As shown in FIGS. 1 to 4, this absorbent article 1 includes the outer cover 2 provided on the exterior side of the absorbent article 1 and the inner cover 3 provided on the skin-facing side of the outer cover 2.

The inner cover 3 includes an absorbent core 4 for absorbing wearer's bodily discharges such as urine, and the like. When worn, this absorbent article 1 is applied to an area including the wearer's crotch region. At this time, the outer cover 2 is applied to an area at least including the wearer's front waist region, rear waist region and crotch region. The inner cover 3 is arranged so as to be applied at least to the wearer's crotch region. The outer cover 2 corresponds to a sheet member according to the present invention.

The outer cover 2 has a front waist region 6, a rear waist region 7 and a crotch region 8 to be applied to the wearer's front waist region, rear waist region and crotch region, respectively. A left edge 6a of the front waist region 6 and a left edge 7a of the rear waist region 7 are joined to each other by predetermined bonding means while facing each other to form a left side joint part 9. A right edge 6b of the front waist region 6 and a right edge 7b of the rear waist region 7 are joined to each other similarly to form a right side joint part 9. Accordingly, the absorbent article 1 is of the garment-type structure having a waist opening 11, and left and right leg openings 12. The bonding means for these side joint parts 9 is, for example, one of ultrasonic welding, heating welding, an adhesive (e.g., a hot melt adhesive) and the like, or a combination of some of them.

The outer cover 2 is formed of two sheets 13 and 14 overlapping each other. These sheets 13 and 14 are bonded together by an adhesive (e.g., hot melt adhesive) with elastic members 21 to 26 to be described later being interposed therebetween.

The sheets 13 and 14 are made of, for example, a liquid-repellent nonwoven fabric of synthetic fibers, a synthetic resin film of polyethylene or the like (a liquid-impermeable and breathable film is preferred), or a laminate of these materials. To reduce dampness, a liquid-repellent nonwoven fabric is preferably employed for at least one of the sheets 13 and 14. The nonwoven fabric may include, but is not limited to, those made of synthetic fibers of polypropylene, polyethylene, polyester or nylon. The nonwoven fabric may include, but is not limited to, composite fibers of polyester and polyester, composite fibers of polyester and polyethylene, or composite fibers of polypropylene and polyethylene. The nonwoven fabric is preferably produced by one of spunbonding, air-through method, point bonding, melt blown method and air laid method, or a combination of some of these techniques. Among others, a long staple nonwoven fabric produced by spunbonding or SMS (Spunbonding/Melt blown/Spunbonding) which is a combination of spunbonding and melt blown method is preferable in view of strength. Most preferred is a long staple nonwoven fabric produced by spunbonding.

The inner cover 3 includes the above-mentioned absorbent core 4, a back sheet 15, a top sheet 16, left and right side sheets 17, and the like. The inner cover 3 is bonded to the skin-facing side of the outer cover 2 by an adhesive (e.g., hot melt adhesive).

The absorbent core 4 is arranged so as to be enclosed by the back sheet 15 on the exterior side, and the top sheet 16 and the side sheets 17 on the skin-facing side. The back sheet 15 is preferably made of a liquid-impermeable material, such as a liquid-repellent nonwoven fabric of synthetic fibers, a synthetic resin film of polyethylene or the like (a liquid-impermeable and breathable film is preferred).

The top sheet 16 is located at a laterally central position on the skin-facing side of the absorbent core 4 to extend in the longitudinal direction Y. The left and right side sheets 17 are arranged in the longitudinal direction Y so as to overlap left and right edges of the top sheet 16 from the skin-facing side. A thread-like elastic member 18 is attached in a stretched state to the laterally inner-side edge of each of the side sheets 17. Contraction of the elastic members 18 causes part of the side sheets 17 to stand up to the skin-facing side to function as standing leg gathers. These standing leg gathers protect against side leakage of bodily discharges.

The absorbent core 4 is formed of an assembly at least having assembled fibers. The absorbent core 4 may be covered by a sheet not shown made of a liquid-permeable nonwoven fabric or the like (in the present embodiment, the absorbent core 4 is covered by a liquid-permeable sheet). The assembly constituting the absorbent core 4 is mainly formed of assembled fibers. For the fibers, fibrillated pulp fibers or cellulosic fibers are mainly employed, into which thermally-welded fibers or the like may be mixed according to necessity. The assembly preferably contains super absorbent polymer powder. Supposing that the fibers and super absorbent polymer powder constitute 100% by mass in total, the super absorbent polymer powder is preferably contained by not less than 20% by mass. The super absorbent polymer powder can ensure excellent absorbing performance, and retains bodily fluids therein, to thereby prevent back flow of the bodily fluids. However, mixing an excessively large amount of super absorbent polymer powder will stiffen the assembly. Accordingly, the super absorbent polymer powder is preferably mixed by not more than 80% by mass, and more preferably, by not more than 60% by mass. For the super absorbent polymer powder, polyacrylate-based one or the like commonly used in this field is preferable.

The assembly constituting the absorbent core 4 may take various forms of plan shape including, but not limited to, sandglass, substantially rectangle and substantially oval. In the present embodiment, the absorbent core 4 (assembly) is of a sandglass plan shape as shown in FIG. 1 having a narrow portion 4a at the longitudinally central position of the absorbent core 4 (corresponding to the wearer's crotch region).

The top sheet 16 is made of a liquid-permeable nonwoven fabric or woven fabric of synthetic fibers. The nonwoven fabric or woven fabric is preferably made of, but not limited to, hydrophilic fibers such as silk, rayon and pulp, or fibers or composite fibers mentioned as exemplary materials for the sheets 13 and 14 of the outer cover 2. To improve liquid permeability, the nonwoven fabric or woven fabric employed for the top sheet 16 may be treated to be hydrophilic. The side sheets 17 are made of a liquid-repellent nonwoven fabric, for example.

Attached to the outer cover 2 are: at least one front waist elastic member 21; at least one rear waist elastic member 22; at least one front body elastic member 23; at least one rear body elastic member 24; at least one front leg elastic member 25; and at least one rear leg elastic member 26. These elastic members 21 to 26 contract at respective portions of the absorbent article 1 including the outer cover 2 to fit to the wearer's body.

The front waist elastic member 21 is attached in a stretched state to the upper edge of the front waist region 6 of the outer cover 2 to extend along the upper edge. The rear waist elastic member 22 is attached in a stretched state to the upper edge of the rear waist region 7 of the outer cover 2 to extend along the upper edge. These waist elastic members 21 and 22 contract in the lateral direction X along the waist hole 11 of the outer cover 2.

The front body elastic member 23 is attached in a stretched state in the lateral direction X to a region of the front waist region 6 of the outer cover 2 to be positioned at the wearer's waist (a longitudinally middle region of the front waist region 6). The rear body elastic member 24 is attached in a stretched state in the lateral direction X to a region of the rear waist region 7 to be positioned at the wearer's waist (a longitudinally middle region of the rear waist region 7). These body elastic members 23 and 24 contract laterally in the longitudinally middle regions of the waist regions 6 and 7, respectively.

The front leg elastic members 25 are attached in a stretched state along a path from the front end of one of the leg-side edges 2a and 2b, crossing the crotch region 2c, and leading to the front end of the other leg-side edge. The rear leg elastic members 26 are attached in a stretched state along a path from the rear end of one of the leg-side edges 2a and 2b, crossing the crotch region 2c, and leading to the rear end of the other leg-side edge. In the present embodiment, there are attached a plurality of (e.g., three) front leg elastic members 25 and a plurality of (e.g., three) rear leg elastic members 26. These leg elastic members 25 and 26 are attached to contract along the left and right leg openings 12 of the outer cover 2 and absorbent article 1 as well as the crotch region.

The leg elastic members 25 and 26 intersect at left and right intersections 27 located in the crotch region 2c. The left and right intersections 27 are placed at any position on the laterally outer side relative to the vicinity of left and right side edges 4b of the absorbent core 4 in the crotch region 2c. More specifically, the center of either intersection 27, indicated by an arrow P1, is located at any position on the laterally outer side relative to the vicinity of either of the left and right side edges 4b (indicated by an arrow P2) of the absorbent core 4. Accordingly, on the laterally inner side relative to the left and right intersections 27, the front leg elastic members 25 and rear leg elastic members 26 are reversed in position. It should be noted that, throughout the description of the present invention, "the laterally outer portions relative to the vicinity of the left and right side edges 4b of the absorbent core 4" means, not only the laterally outer portions relative to the left and right side edges 4b, but also the laterally inner portions in the vicinity of the left and right side edges 4b.

More specifically, according to the present embodiment, the center (P1) of either intersection 27 is positioned on the laterally outer side relative to the vicinity of either of the left and right side edges 4b (P2) in the narrow portion 4a of the absorbent core 4. In this respect, a variation will be described later with reference to FIG. 5.

The front leg elastic members 25 have left and right front leg contraction-reduced sections 28 reduced in contractile force by cutting up, on the laterally outer side relative to the intersections 27. The rear leg elastic members 26 have left and right rear leg contraction-reduced sections 29 reduced in contractile force by cutting up, on the laterally outer side relative to the intersections 27. These leg contraction-reduced sections 28 and 29 are formed as follows. First, the elastic members 25 and 26 are attached to the outer cover 2 in a stretched state along the predetermined paths as mentioned above. Then, the elastic members 25 and 26 are each cut up at one or several positions in certain portions thereof, to thereby weaken their contractile forces.

In the present embodiment, as shown in FIGS. 1 and 4, the intersections 27 of the elastic members 25 and 26 are located at a position (P4) shifted toward the front side by a predetermined distance D1 from the longitudinally central position P3 of the absorbent article 1 in an open state.

The elastic materials (e.g., elastic threads) constituting the elastic members 21 to 26 include, but are not limited to, elastic stretchable materials (polyurethane threads, natural rubber, or the like) widely employed for absorbent articles. Alternatively, a band-like polyurethane film may be employed for the elastic materials.

The elastic members 21 to 26 are located between the two sheets 13 and 14 constituting the outer cover 2, as described above. Bonding of the sheets 13 and 14 to each other and bonding of the elastic members 21 to 26 to the sheet members 13 and 14 are achieved by using bonding means such as an adhesive (e.g., hot melt adhesive), heating welding, ultrasonic welding or the like. For example, as the elastic members 21 to 26, polyurethane threads of 300 to 2000 decitex are stretched 1.1 to 5.0 times their original length to be sandwiched between the sheets 13 and 14.

As described above, the present embodiment provides the absorbent article 1 that exerts effective contraction on the crotch region while relaxing appropriately the degree of contraction along the leg-side edges, facilitates pulling up and down, and allows the left and right portions of the crotch region to fit appropriately to the wearer's crotch region, as will be described below.

More specifically, according to the present embodiment, at least one front leg elastic member 25 is attached in a stretched state along the path from the front end of one of the leg-side edges 2a and 2b, crossing the crotch region 2c, and leading to the front end of the other leg-side edge. Similarly, at least one rear leg elastic member 26 is attached in a stretched state along the path from the rear end of one of the leg-side edges 2a and 2b, crossing the crotch region 2c, and leading to the rear end of the other leg-side edge. The elastic members 25 and 26 intersect at the left and right intersections 27 located in the crotch region 2c. Accordingly, the lateral contractile force of the elastic member 25 and that of the elastic member 26 cooperate together to act upon the crotch region 2c.

Particularly, according to the present embodiment, the left and right intersections 27 are placed at any position on the laterally outer side relative to the vicinity of the left and right side edges 4b. The contraction of the elastic members 25 and 26 is less likely to act effectively upon the fibrous assembly constituting the absorbent core 4 due to the high rigidity of the assembly. Therefore, in the crotch region 2c of the absorbent article 1, the contraction effect of the elastic members 25 and 26 in the lateral direction X is expected to act particularly upon the laterally outer portions relative to the vicinity of the left and right side edges 4b. In this respect, the present embodiment allows the lateral contraction of the elastic members 25 and 26 to act effectively upon the laterally outer portions relative to the vicinity of the left and right side edges 4b in the crotch region 2c of the absorbent article 1.

Accordingly, the portions of the elastic members 25 and 26 located in the crotch region 2c exert sufficient lateral contraction on the crotch region 2c. This in result can prevent the crotch region of the absorbent article 1 from become widened in the lateral direction X, allowing the left and right leg openings 12 to be enlarged. This allows the wearer to insert his/her legs easily into the leg openings 12, which facilitates pulling up and down of the absorbent article 1. In addition, the prevention of lateral widening of the crotch region 2c reduces a wearer's discomfort at the crotch region.

Again, according to the present embodiment, the front and rear leg elastic members 25 and 26 are provided with the left and right contraction-reduced sections 28 and 29, respectively, on the laterally outer side relative to the intersections 27. The presence of these leg contraction-reduced sections 28 and 29 at the four positions relaxes appropriately the degree of contraction of the leg elastic members 25 and 26 along the leg-side edges of the absorbent article 1, which in result can prevent excessive shrinkage of the leg openings 12. This allows the wearer to insert his/her legs easily into the leg openings 12, which facilitates pulling up and down of the absorbent article 1. In addition, the appropriate relaxation of contraction of the leg elastic members 25 and 26 provides the wearer with a soft fit.

Further, according to the present embodiment, the leg elastic members 25 and 26 intersect at the left and right intersections 27 located in the crotch region 2c, and the intersections 27 are located at any position on the laterally outer side relative to the vicinity of the left and right side edges 4b of the absorbent core 4. This allows the elastic members 25 and 26 to exert their contractile forces effectively upon the left and right portions of the crotch region of the absorbent article 1 (particularly on the laterally outer portions relative to the vicinity of the left and right side edges 4b). As a result, the left and right portions of the crotch region of the absorbent article 1 fit appropriately to the wearer's crotch region. Therefore, clearances that may cause leakage of bodily discharges such as urine therethrough are less likely to be formed between the left and right portions of the crotch region of the absorbent article 1 and the wearer's crotch region.

As described, according to the present embodiment, the left and right intersections 27 at which the leg elastic members 25 and 26 intersect are located at any position on the laterally outer side relative to the vicinity of left and right side edges 4b of the absorbent core 4. This ensures that the leg elastic members 25 and 26 exert contraction on the portions of the crotch region of the absorbent article 1 where contraction of the leg elastic members 25 and 26 is particularly effective (i.e., on the laterally outer portions relative to the vicinity of the left and right side edges 4b).

As described, according to the present embodiment, the absorbent core 4 is provided for the inner cover 3 located on the skin-facing side of the outer cover 2. Accordingly, the absorbent article 1 of high quality can be obtained that avoids disadvantages such as the absorbent core 4 obstructing or being damaged while applying the elastic members 21 to 26 (particularly, the leg elastic members 25 and 26) to the outer cover 2, while forming the leg contraction-reduced sections 28 and 29 in the leg-side elastic members 25 and 26, and the like.

Figure 5:
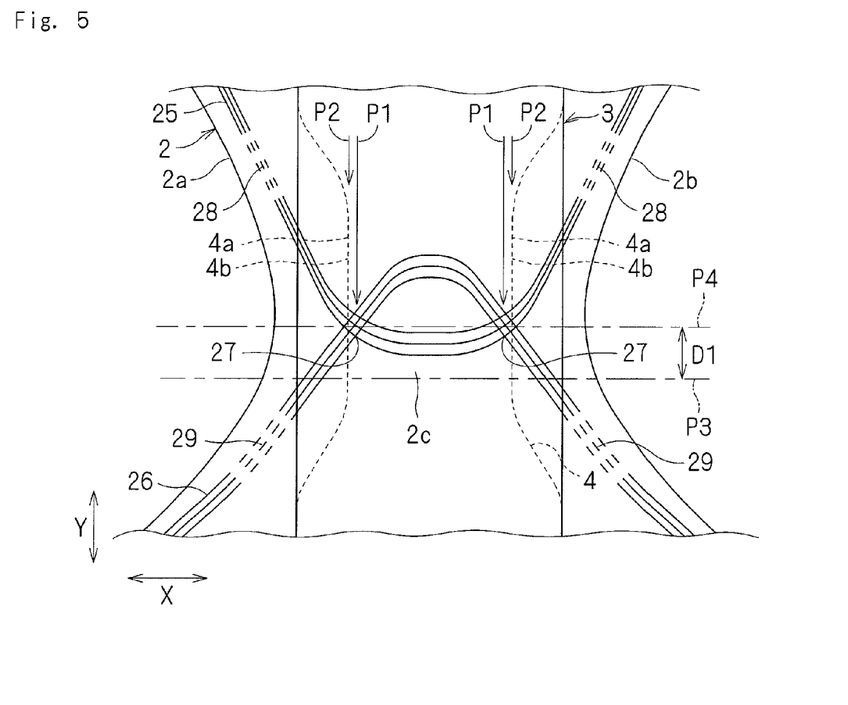
FIG. 5 illustrates a variation of the structure shown in FIG. 4.

FIG. 5 shows a structure as a variation of the present embodiment relating to the position of the left and right intersections 27. In the structure shown in FIG. 5, the center (P1) of either intersection 27 is located on the laterally inner side in the vicinity of either of the left and right side edges 4b (P2) of the absorbent core 4 in the crotch region 2c. In the structure shown in FIG. 5, the leg elastic members 25 and 26 are attached to the outer cover 2 along different paths from those shown in FIGS. 1 and 4. The structure shown in FIG. 5 achieves substantially similar effects to those of the above-described first embodiment.

Figure 6:
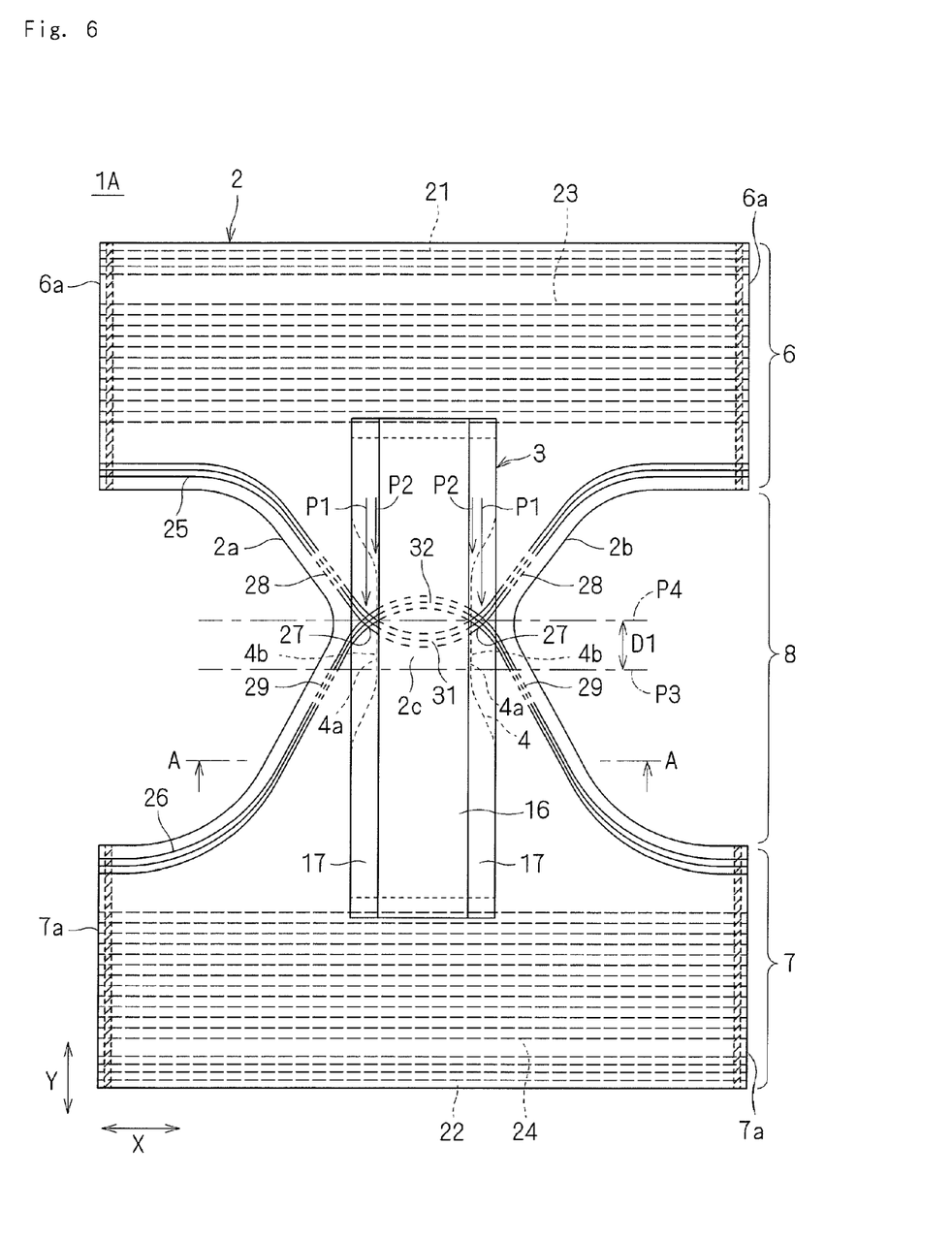
FIG. 6 is a plan view of a disposable absorbent article according to a second embodiment of the present invention, substantially in a flat-out, open state with left and right side joint parts separated.
Figure 7:
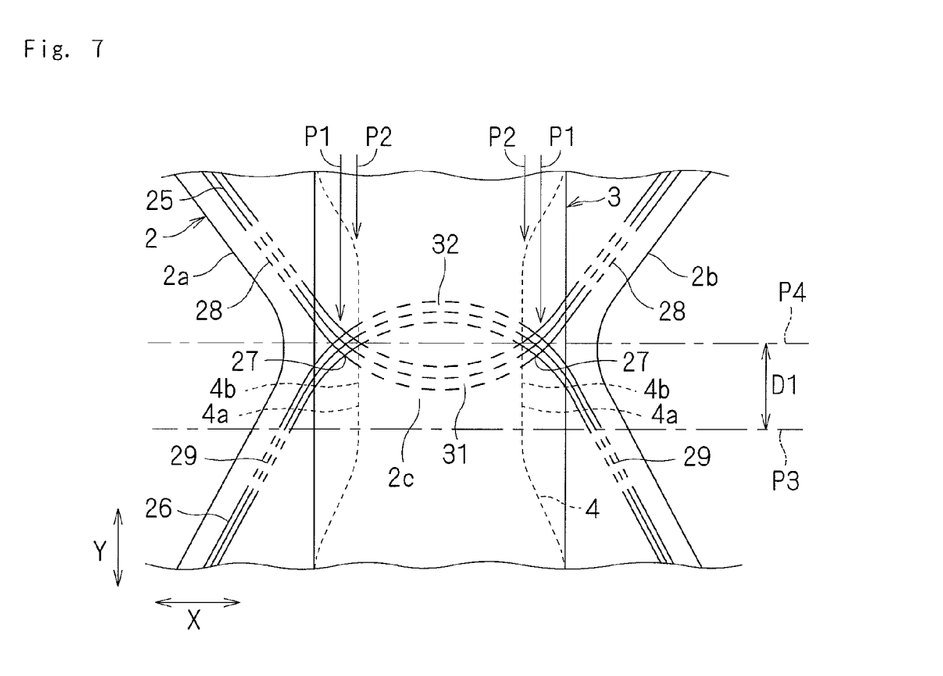
FIG. 7 is a partially enlarged view of the structure shown in FIG. 6.

FIG. 6 is a plan view of an absorbent article 1A according to a second embodiment of the present invention, substantially in a flat-out, open state with left and right side joint parts separated. FIG. 7 is a partially enlarged view of the structure shown in FIG. 6. The absorbent article 1A according to the present embodiment substantially differs from the absorbent article 1 according to the first embodiment only in that the leg elastic members 25 and 26 are additionally provided with first and second crotch contraction-reduced sections 31 and 32. Accordingly, components of the structure according to the present embodiment common to those of the first embodiment are indicated by the same reference numerals, and description thereof will not be repeated.

In the absorbent article 1A according to the present embodiment, as shown in FIGS. 6 and 7, the leg elastic members 25 and 26 are provided with the first and second crotch contraction-reduced sections 31 and 32, respectively, in addition to the leg contraction-reduced sections 28 and 29. These crotch contraction-reduced sections 31 and 32 are located at any position between the left and right intersections 27. In the present embodiment, the crotch contraction-reduced sections 31 and 32 range respectively over the entire portions of the leg elastic members 25 and 26 that are located on the laterally inner side relative to the vicinity of the left and right side edges 4b. The leg elastic members 25 and 26 are cut up to reduce their contractile forces to form the crotch contraction-reduced sections 31 and 32, respectively. The crotch contraction-reduced sections 31 and 32 are formed by substantially the same technique of forming the leg contraction-reduced sections 28 and 29.

With this structure, the present embodiment achieves substantially similar effects to those of the first embodiment, as well as the following specific effects. More specifically, the presence of these crotch contraction-reduced sections 31 and 32 more effectively relaxes the contractile forces exerted on the crotch region of the absorbent article 1A (particularly on the laterally inner portion relative to the vicinity of the left and right side edges 4b). Disadvantages can therefore be avoided such as twisting of the crotch region of the absorbent article 1A and excessive contractile forces exerted on the absorbent core 4 that may reduce the absorbing capability of the absorbent core 4.

Further, the leg elastic members 25 and 26 exert their contractile forces together at the left and right intersections 27. This can maintain the contracting function upon the left and right portions of the crotch region of the absorbent article 1A (particularly on the laterally outer portions relative to the vicinity of the left and right side edges 4b), while, as described above, effectively relaxing the contractile forces exerted on the crotch region of the absorbent article 1A (particularly on the laterally inner portion relative to the vicinity of the left and right side edges 4b).

Furthermore, the first and second crotch contraction-reduced sections 31 and 32 range respectively over the entire portions of the leg elastic members 25 and 26 that are positioned on the laterally inner side relative to the vicinity of the left and right side edges 4b. This ensures relaxation of the contractile forces exerted on the portion where the absorbent core 4 is located in the crotch region of the absorbent article 1A. Disadvantages can therefore be avoided with more reliability such as twisting of the crotch region of the absorbent article 1A and excessive contractile forces exerted on the absorbent core 4 that may reduce the absorbing capability of the absorbent core 4.

Figure 8:
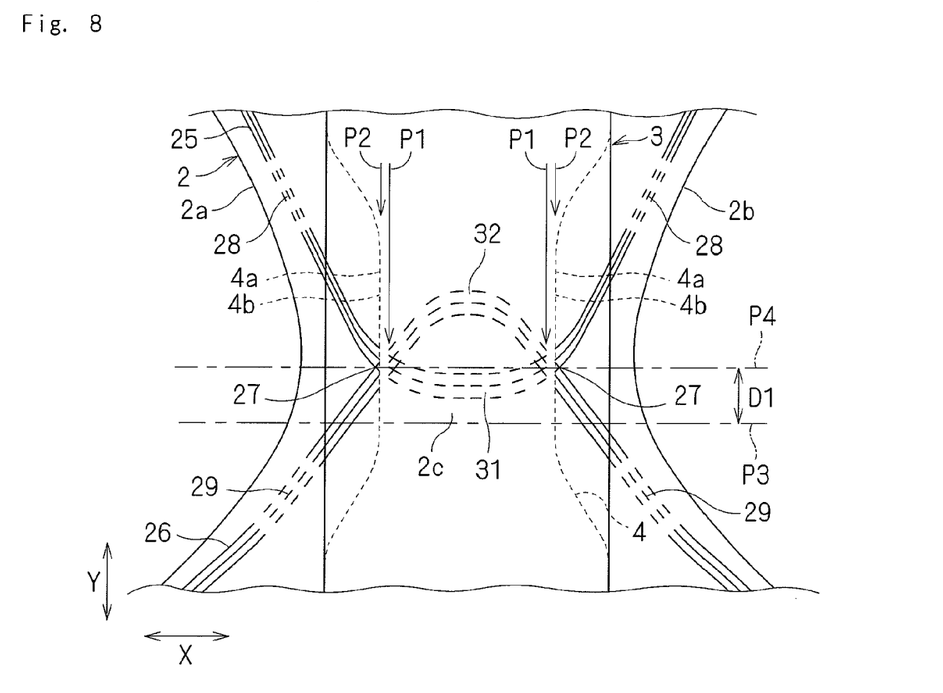
FIG. 8 illustrates a variation of the structure shown in FIG. 7.

As a variation of the structure described in the second embodiment, as shown in FIG. 8, the crotch contraction-reduced sections 31 and 32 may be added to the structure shown in FIG. 5. In the structure shown in FIG. 8, the center (P1) of either intersection 27 of the leg elastic members 25 and 26 is positioned on the laterally inner side in the vicinity of either of the left and right side edges 4b (P2) of the absorbent core 4 in the crotch region 2c. Accordingly, the crotch contraction-reduced sections 31 and 32 each overlap the laterally inner portion of the left and right intersections 27. This structure shown in FIG. 8 also provides substantially similar effects to those of the structure according to the second embodiment.

While the absorbent core 4 is provided in the inner cover 3 in the first and second embodiments, the absorbent core 4 may be provided for the outer cover 2. In this case, the absorbent core 4 may be sandwiched between the sheets 13 and 14 of the outer cover 2, or may be attached to the skin-facing side of the outer cover 2, for example. In this case, the inner cover 3 may be eliminated.

In the above-described first and second embodiments, the technique according to the present invention is applied to the garment-type absorbent articles 1 and 1A, respectively. However, the technique according to the present invention may also be applied to a hook-and-loop-type disposable diaper.

While the present invention has been described in detail, the above description is in every aspect illustrative, and the present invention is not limited thereto. It should be appreciated that numerous variations not illustrated herein can be made without departing from the scope of the present invention.

What is claimed is:

1. A disposable absorbent article for being applied to a region including a crotch region of a wearer, the disposable absorbent article comprising:
   a sheet member to be applied to a region at least including a front waist region, the crotch region and a rear waist region of the wearer;
   an absorbent core provided inside said sheet member or on a skin-facing side of said sheet member for absorbing bodily fluids discharged from the wearer, said absorbent core having a left side edge and a right side edge;
   at least one front leg elastic member attached in a stretched state along a path from a front end of one of left and right leg-side edges of said sheet member, crossing a crotch region of said sheet member, and leading to a front end of the other of said left and right leg-side edges; and
   at least one rear leg elastic member attached in a stretched state along a path from a rear end of one of said left and right leg-side edges of said sheet member, crossing said crotch region of said sheet member, and leading to a rear end of the other of said left and right leg-side edges,
   wherein said front leg elastic member and said rear leg elastic member intersect at a left intersection and a right intersection, each of said left intersection and said right intersection being located in said crotch region of said sheet member, and a center of each of said left intersection and said right intersection being located at a position between said left side edge and said right side edge of said absorbent core in a lateral direction,
   wherein said front leg elastic member has left and right front leg contraction-reduced sections located outwardly of said left and right intersections in the lateral direction, said left and right front leg contraction-reduced sections being cut so as to have reduced contractile forces, and
   wherein said rear leg elastic member has left and right rear leg contraction-reduced sections located outwardly of said left and right intersections in the lateral direction, said left and right rear leg contraction-reduced sections being cut so as to have reduced contractile forces.

2. The disposable absorbent article according to claim 1, wherein said front leg elastic member further includes a first crotch contraction-reduced section located between said left and right intersections, said first crotch contraction-reduced sections being cut so as to have reduced contractile forces, and wherein said rear leg elastic member further includes a second crotch contraction-reduced section located between said left and right intersection, said second crotch contraction-reduced sections being cut so as to have reduced contractile forces.

3. The disposable absorbent article according to claim 2, wherein said first crotch contraction-reduced section extends over an entirety of said front leg elastic member between said left side edge and said right side edge of said absorbent core, and wherein said second crotch contraction-reduced section extends over an entirety of said rear leg elastic member between said left side edge and said right side edge of said absorbent core.

4. The disposable absorbent article according to claim 1, further comprising an inner cover provided on the skin-facing side of said sheet member to be applied at least to the crotch region of the wearer, wherein said absorbent core is provided in said inner cover.

5. The disposable absorbent article according to claim 1, wherein said sheet member forms a waist opening and left and right leg openings when joining a left edge of a front section and a left edge of a rear section, and joining a right edge of said front section and a right edge of said rear section.

* * * * *